United States Patent [19]

Findlay

[11] Patent Number: 5,037,749

[45] Date of Patent: Aug. 6, 1991

[54] POROUS IMMOBILIZATION SUPPORT PREPARED FROM ANIMAL BONE

[75] Inventor: Christopher J. Findlay, Cambridge, Canada

[73] Assignee: Protein Foods Group Inc., Hamilton, Canada

[21] Appl. No.: 624,960

[22] Filed: Dec. 10, 1990

Related U.S. Application Data

[63] Continuation-in-part of Ser. No. 343,767, Apr. 27, 1989, abandoned, which is a continuation-in-part of Ser. No. 887,393, Jul. 21, 1986, abandoned, which is a continuation-in-part of Ser. No. 753.286, Jul. 9, 1985, abandoned.

[30] Foreign Application Priority Data

| Jul. 8, 1986 | [EP] | European Pat. Off. | 86630112.0 |
| Jul. 9, 1986 | [CA] | Canada | 513418 |
| Jul. 9, 1986 | [JP] | Japan | 61-159883 |

[51] Int. Cl.$^5$ .................... C12N 11/14; C12N 11/02; A22C 25/16; G01N 33/551
[52] U.S. Cl. .................... 435/176; 435/177; 436/524; 436/528; 530/811; 530/812
[58] Field of Search .......... 435/174, 176, 177; 17/46; 530/811, 812; 436/524, 528

[56] References Cited

U.S. PATENT DOCUMENTS

| 3,519,538 | 7/1970 | Messing et al. | 530/811 X |
| 3,594,190 | 7/1971 | Eslinger et al. | 17/46 X |
| 4,092,219 | 5/1978 | Lin et al. | 435/177 X |
| 4,232,425 | 11/1980 | Wojcik | 17/46 |
| 4,248,969 | 2/1981 | Lee | 435/176 |
| 4,279,058 | 7/1981 | Ivey | 17/46 |
| 4,340,184 | 7/1982 | Poss | 241/82.3 |
| 4,421,850 | 12/1983 | Daniels et al. | 435/177 X |
| 4,473,589 | 9/1984 | Freeman et al. | 435/68.1 X |

*Primary Examiner*—David M. Naff
*Attorney, Agent, or Firm*—Rogers & Scott

[57] ABSTRACT

Porous immobilization support materials for use in physical and chemical processes are produced from bird, animal or fish bone by cleaning finely divided bone to remove all external tissue and by dissolving away all internal tissue from internal pores and internal Haversian canals of the bone to result in cleaned bone containing not more than 0.5% by weight of remaining lipid material, preferably containing only trace amounts, i.e. less than 0.1% by weight. The cleaned bone consists of porous finely-divided animal bone containing a collagenous matrix of organic fibrous connective tissue material including osein having uniformaly distributed therethrough mineral hydroxyapatite. The collagenous matrix provides an ideal distributed site for the chemical attachment of bacteria, cells and enzyme catalysts. The attachment may be by absorption, or by charge attraction, or with a cross-linking agent attachable between the bone and the supported material. An economical source of bone is a boney fraction from mechanical separation of meat and bone such as in recovering meat from chicken necks and backs unwanted by the chicken fast food industry. Chicken bone is more porous than other animal bone and is particularly suitable for immobilization.

29 Claims, No Drawings

POROUS IMMOBILIZATION SUPPORT PREPARED FROM ANIMAL BONE

CROSS-REFERENCE TO RELATED APPLICATIONS

This application is a continuation-in-part of my prior application Ser. No. 07/343,767, filed 27th Apr. 1989, now abandoned, which is a continuation-in-part of my prior application Ser. No. 06/887,393, filed 21st July 1986, now abandoned, which is a continuation-in-part of my prior application Ser. No. 06/753,286, filed 9th July 1985, now abandoned.

FIELD OF THE INVENTION

The present invention is concerned with new immobilization support materials for chemical and physical processes, and methods of making such new support materials.

REVIEW OF THE PRIOR ART

Increasingly many modern chemical processes require the employment of immobilization support materials, for example, for the support of catalysts employed in a chemical reaction. An example of physical processes requiring a support material are the various types of chromatography in which a column of support material selectively retains compounds from the fluid flowing through it, and subsequently the retained material is viewed or removed for assay. The effective support of catalysts has become increasingly important with the employment of catalysts which are cells or bacteria, or complex chemical substances, specific examples the latter being enzymes which are usually complex protein molecules. At least in commercial and pilot plant production, and advantageously in laboratory practice, a support material must be provided for the catalyst which will maximize the surface available for catalytic activity, and will also retain the catalyst against physical removal by the flowing reacting materials, so as to provide for fast efficient reaction with minimum loss of the catalyst. Secure retention is usually needed to prevent undesirable contamination of the product with the catalyst. In the art this is referred to as immobilization of the catalyst on the support material. Most important is the overall cost of immobilization which includes the effective cost of the support material, the enzyme, and the immobilization procedure.

Typical support materials that have been used hitherto are polymer gels (for example, alginates, agaroses and polyacrylamides) and cell wall material, but these are relatively soft materials that are not able to withstand high pressures and/or high flow rates of the chemical reactants over and/or through them without disruption and physical loss of the catalyst. Thus, if the rate of flow of the reacting materials is too high the catalyst is quickly exhausted by physical loss and continuous production is not possible, while if the rate is kept sufficiently low for this not to happen relatively large quantities of support and catalyst must be employed, with correspondingly large reactor vessels and high capital costs. It is of course possible to provide polymer gel support materials of higher mechanical strength by increasing the internal polymer cross-linking so that more solid materials are obtained, but such materials are less pervious and also have a special problem of the potential toxicity of any residual monomer, or residual low molecular weight polymer, requiring expensive toxicological assessment before the particular batch can be employed.

Another product that has been used for catalyst support is porous glass beads of controlled pore size, the catalyst being immobilised thereon by covalent bonding; it has been found that this type of support material has difficulty with inactivation of some important enzymatic catalysts (e.g. lactose) and with treatment of fluid suspensions including particles larger than the pore size (e.g. fluid milk) with extensive fouling of the pores.

U.S. Pat. No. 4,572,897 issued 25th Feb. 1986 to Novo Industri A/S discloses a carrier for immobilizing enzymes consisting of hydrophilic binder material, such as polyvinyl alcohol, polyvinyl pyrrolidone; numerous cellulose derivatives, notably carboxy methyl cellulose, hydroxyethyl cellusoe, hydroxypropyl cellulose, methyl cellulose and ethyl cellulose; naturally occurring polysaccharides including agar, alginate, chitosan and starch; and proteins including gelatine, soy protein, albumen, zein, casein, gluten and protein hydrolysates. The hydrophilic binder material is formed as granules and the enzyme is bound to the binder material at the granule surface; the binder material is extended and formed as these granules through the use of an inert filler, consisting of a multitude of discrete, hard and inert water insoluble particles that are inert to the binder, to the enzyme and to all ingredients in the enzymatic reaction medium, including the medium itself. A large number of filler materials are suggested including bone meal, although the preferred fillers are diatomaceous earth and cellulose fibre.

Bone meal is defined in the Condensed Chemical Dictionary, 8th Edition, published 1971 by Van Nostrand Reinhold Company as a product made by grinding animal bones. Raw meal is disclosed as used as a fertilizer and is made from bones that have not been previously steamed, so that it will still include adipose tissue, and internal and external membrane. Steamed bone meal is disclosed as used for animal feed and may be pressure steamed, and such steaming will reduce the amount of adipose tissue but will not remove the internal and external membrane.

U.S. Pat. No. 4,232,425 (Wojcik) issued 11th Nov. 1980 to Darling & Company discloses a method of producing low fat stabilized bone as an intermediate stage in the production of high quality gelatine, namely crushed bone of a size within the selected range preferred for making such gelatine; there is no suggestion that the resultant bone material is to be used for other than gelatine production. The process is intended to provide bone material which when held for a prolonged period does not develop objectionable odors, does not discolor and is not attacked by bacteria, fungus or similar microorganisms. The foregoing criteria require, for bone intended for use in producing high quality gelatine without fat interference, that it be substantially free of adhering meat tissue and have a low fat content (i.e. a maximum fat content of 3% by weight), even though bone can be stablized with a higher fat content (i.e. up to 10% by wt.). The bone material must also be heated during processing to effect stabilization, preferably when removing moisture, to a temperature above 180° F. (82° C.) to produce a "kill temperature" for any microorganisms which may contaminate the raw bone and to simultaneously reduce the moisture content of the bone to a maximum of 12% by weight and preferably below 10% by weight, so that growth of microorganisms will not be supported. The process of the invention is adapted to provide a continuous and essentially automated process of producing clean stabilized bone of high quality from raw bone material of various sources but which will have varying amounts of fat, meat and the like organic tissue adhering thereto, remaining in its pores, or admixed therewith. To this end the raw bone is heated to crisp the fat and meat tissue adhering thereto, so that they are more readily removed from the particles of bone during processing; but care is to be exercised to avoid using such elevated temperatures or prolonged retention times which result in burning or scorching the raw bone material so that the stabilized product has a clean light color rather than having a dark discolored appearance as a result of "burning off" of surface fat. The pieces of bone with adhering pieces of crisp fat and meat tissue are then subjected to a dry separation treatment comprising screening to a selected particle size range and gravity separation such as on an inclined vibrating screen air table, which is stated to remove substantially all of the residual crisped residual fat and meat tissue. Such a process will not remove the internal membrane material from the pores of the bone. The product when produced from raw trimmed beef bones is stated to have as a typical composition 4.65% moisture, 29.05% protein, 61.68% ash and 2.49% fat, all on a weight basis, while 500 ton production lots are stated to have average composition values of 3.72% moisture, 30.0% protein, ash content 63.5% and 1.78% fat.

U.S. Pat. No. 4,340,184, issued 20th July 1982 to Poss Design Limited discloses apparatus for the gross separation of meat and bone resulting in a meat fraction of low bone content (i.e. 1% by weight or lower) and a bone fraction of relatively high meat content (i.e. about 25% by weight). The further processing of the bone fraction is not discussed.

U.S. Pat. No. 4,421,850, (Daniels et al), issued 20th Dec. 1983 to Tate & Lyle Limited, discloses an immobilized enzyme support material for enzyme products wherein the active immobilized enzyme is made part of an external gel layer mounted on the support material. The gel layer may be made for example by contacting the inner support material with an aqueous solution of the enzyme and with a water-miscible organic solvent and thereafter contacting the externally coated support material with a cross linking agent to gel the resultant coating. One the materials suggested for the support material is hydroxyapatite spheroids while the preferred material is bone char, otherwise known as bone black, bone charcoal or animal charcoal. The bone char is characterized as comprising a hydroxyapatite structure over which there is a thin, evenly-dispersed coating of active carbon. The supported material is to be carried predominately on the outside surface of the support in the form of the gel coating, but it is stated that nevertheless pores appear to be of benefit. Glutaraldehyde is suggested as a cross-linking agent to gel the mixture of the solution of enzyme with organic solvent. A physical description of the bone char is given that it consists of a residual matrix of hydroxyapatite with the protein component completely pyrolised to the extent that it is left as a coating of active carbon, and accordingly provides only a physical support for the gelled coating of active material.

DEFINITION OF THE INVENTION

In accordance with the present invention there is provided new immobilizing support materials for use in chemical or physical processes for the support of supported material, consisting of finely-divided animal bone from the external surfaces of which the external tissue has been removed, and from the internal surfaces of which, namely the surfaces of the internal pores and Haversian canals, the internal tissue has been removed by dissolving it therefrom, to result in cleaned bone containing not more than 0.5% by weight of remaining lipid material, wherein the collagenous matrix is exposed and provides sites for the support of material to be supported.

Also in accordance with the invention there is provided a method of making immobilization support material for the support of supported material for chemical and physical processes, comprising removing external tissue from the external surfaces of finely divided animal bone, and dissolving internal tissue from the internal surfaces of the bone, namely the surfaces of the internal pores and Haversian canals, to result in cleaned bone containing not more than 0.5% by weight of remaining lipid material, wherein the collagenous matrix is exposed to provide sites for the support of material to be supported.

Preferably, with the immobilization support materials of the invention, and with the methods of the invention, the finely divided animal bone is cleaned until it contains not more than a trace of remaining lipid material, i.e. not more than 0.1% by weight.

The cleaned finely-divided bone may be provided with a cross-linking agent for the material to be retained on the support material. The cross-linking agent is, for example, a bi-functional compound able to attach itself securely to the collagenous matrix of the bone and to the material to be retained. A suitable cross-linking agent for enzymatic catalyst support material is, for example, glutaraldehyde which provides a reactive aldehyde group for attachment of the supported enzyme.

DESCRIPTION OF THE PREFERRED EMBODIMENTS

Bone is a unique natural, mechanically-strong, abundant, non-toxic, composite structural material, which despite the animal family from which it is obtained (e.g. mammals, birds and fishes) consists of a matrix of a relatively stable organic fibrous connective collagenous tissue material, particularly the protein osein, having uniformly distributed therethrough a relatively inert mineral filler of calcium phosphate, in the form of micro-crystalline hydroxyapatite that is insoluble at physiological pH values. A protein-carbohydrate complex called the ground substance surrounds the collagenous fibres. A fourth major constituent is bone-inhabiting cells (osteocytes) each of which occupies its own cavity in the matrix.

Bone in vivo requires a blood supply for its survival, in that, as described in "Structure and Development of Meat Animals" by H. J. Swatland, published 1984 by Prentice-Hall, Inc. the osteocytes can only survive if they develop long cytoplasmic (membrane-coated) extensions which radiate from the lacunae to blood vessels where exchange by diffusion can take place. These cytoplasmic extensions run through fine tubes or canaliculi in the matrix, but these are limited in length. Consequently, large numbers of blood vessels permeate the matrix. Most of these blood vessels run longitudinally through the bone in large Haversian canals which are surrounded by concentric rings of osteocytes and bone lamallae. This porous internal structure produced by the network of fine tubes and canals is lined with a coating consisting of lipo-protein tissue membrane. Bones are also covered by an external connective tissue membrane called the periosteum.

A porous matrix as provided by bone, consisting of uniformly distributed collagen and hydroxyapatite, forms an excellent medium for the immobilization of different types of catalysts, particularly catalyst-containing cellular material and proteinaceous catalysts such as enzymes, which can readily be attached by surface adsorption, charge attraction, or chemically by use of suitable cross-linking agents. Thus, for chemical attachment the high collagen content yields a correspondingly relatively high level of amino acids, residues and particularly carboxyl groups, which facilitate the attachment. Since in this case the bonding is chemical the immobilization is likely to be more stable than with surface adsorption or charge attraction, so that the catalyst is not readily removed by physical action of the reacting solutions. Moreover, the catalyst is more likely to have sterically available active sites, so that it is more active than when physically immobilized on an inert support material, such as a gel or glass beads.

The meat processing industries produce bone as a by-product much of which is not easily disposable. Much of the animal bone is cleaned of most if not all of the external tissue but without removal of the internal tissue and then ground to bone meal for use as animal feed or fertiliser. Another source is the poultry processing industry, especially for fast food restaurants, which has as a by-product large quantities of chicken necks and backs. The processing of these necks and backs for mechanical removal of as much as possible of the usable meat has become a standard practice and results in the production of separate meat and bony fractions, the latter consisting of about 60–70% by weight of finely-divided bone interspersed with unseparated meat, fat, connective tissue, etc. Such processes and apparatus are described in U.S. patent Ser. No. 4,340,184 referred to above. Typically the meat will be of particle size less than about 850 microns, while the bone will be of particle size greater than about 850 microns. This pre-separated bony fraction is therefore an excellent and readily-available source of already finely-divided bone.

Owing to the large quantity of non-bony material present the bony fraction is first thoroughly washed with hot water to remove as economically as possible as much as possible of this non-bony material in a form in which the useful proteins and fats can easily be recovered. For example, the material will be washed with 2–5 volumes of water at a temperature in the range 70° C. to 95° C. The bone support material of the invention is then obtained from such a pre-washed bone fraction by dissolving away both external and internal tissue, this being effected for example by washing each volume of bony fraction with two volumes of caustic soda of 1% concentration at 100° C., the mixture being suitably agitated for a period of about 8 minutes and the resulting extract removed for further processing, again to recover the useful protein and fat. Such a dissolving wash must be sufficient to not only remove all external adipose tissue and membrane, but penetrate into the pores of the finely divided bone and remove the internal membrane and other tissue so that the collagen mineral matrix is exposed. This removal of the internal membrane is essential in that it is the highly porous nature of the bone that enables it to provide a such a relatively large surface area of the collagen matrix for attachment. Other different concentrations (usually in practise in the range 0.25% to 10%) and corresponding suitable periods of washing can be used. The temperature employed can be in the range for example from 20° C. to 120° C.

The cleaning to which the base material is subjected is such as to ensure that any small amount of lipid material (and also carbohydrate material, as will be explained below) that remain will not deleteriously effect the storage life of the support material and/or the processes in which the support material is employed. In particular, the quantity of any remaining lipid material preferably is reduced to trace amounts, which in this field is considered to be less than 0.1% by weight. The reason for this relatively complete cleaning is that endogenous lipids are not inert and have large surface areas, with the consequent high possibility of becoming rancid and smelling and thereby interfering with the processes in which the support material is employed, particularly food processes. There are however non-food processes with which somewhat higher percentages of up to 0.5% by weight could be tolerated, provided that again there is no uneconomic interference with processes involved. The presence of residual carbohydrates, which will usually be in the form of glycoproteins, is usually less deleterious since they are less reactive than lipids and are less likely to interfere with the subsequent immobilization processes; nevertheless the amount present should also be maintained at less than 0.5% by weight, preferably at less than trace amounts of less than 0.1%, so that the total of lipid and carbohydrate materials together are less than 1.0% by weight, and preferably are less than 0.2% by weight. Cleaning processes that will remove the fat content to the low level required will usually also provide adequate removal of the carbohydrates. The extent of the cleaning procedure required also depends upon the animal origin of the bone in that, for example, the somewhat less-porous and large-pored beef bones are more readily cleaned of the internal tissue than are more highly porous chicken bones.

It is found for example that a fish bony fraction requires an alkaline wash of only 2 minutes duration at 100° C., and a longer wash will begin to also dissolve the collagen, while a lamb fraction requires a longer wash of about 15 minutes and a pork or beef fraction requires a still longer wash of about 20 minutes. As described above, and depending upon the specific composition of the bony fraction it may be subjected to a hot water wash prior to the dissolving wash with caustic soda to remove and render fat and proteins that are readily removed by such simple treatment, so as to reduce the amount of alkali that is required. Again, if the alkali treatment alone does not effect sufficient removal by solution of the unwanted tissue, it may be subjected to prior or post enzymatic treatment to hydrolyse it and render it more readily soluble.

The treatment with strong alkali also has the advantage that it sterilises the resultant support material and renders it free of potential reproduction factors such as viruses, bacteria and cells, and also removes potential feed stocks for such factors, such as amino acids. Because the product of this treatment is sterile and relatively stable it can now be stored (e.g. for periods up to one year) in a brine solution (e.g. 20% by weight sodium chloride) or it may be dried by any suitable technique to a moisture content of about 10% or less (preferably 5% or less) and stored for even longer periods. Another advantage for some of the immobilization procedures for which the support material is to be used is that the alkaline treatment leaves the support material positively surface charged, so that it is inherently ready to accept and immobilize a negatively charged supported component.

The mechanically-separated bone that is obtained from this particular source is already finely-divided and after cleaning in accordance with the invention is suitable for use immediately as an immobilization support material. The bone particles from the separation are frequently of about 0.5 cm size, and slivers of up to 4 cm length also occur. In many processes it will be preferred for the support material to be of smaller particle size and the bone may be ground to the required size. A preferred range of sizes for the bone particles is 100 microns (0.1 mm) to 2 mm. Processes employing the support material in the form of a fluidised bed will require the particle size to be in a specific uniform range, for example 1 to 2 mm, and this can be achieved by grinding and sieving. It may also be preferred for the bone to be of larger particle size, e.g. to pass through a 4 mesh screen, especially when it is required to fill a large reactor. Other processes may of course produce finely divided bone of other size ranges and distribution. Bone is a natural, non-toxic, degradable material that is acceptable within quite wide limits as to particle size and volume content as a food constituent, so that it is more widely applicable to food processing systems. Thus, finely divided bone is already approved for use as a source of calcium in various food and vitamin supplements.

In a specific example, an assay of chicken bone fraction material from such a mechanical separator showed the following composition, expressed as approximate percentages by weight:

| Fat: | 8% | |
| Protein: | 17% | (Collagen 8%) |
| Bone: | 30% | (Calcium 8%) |
| Water: | 45% | |

One hundred (100) parts of the mixture was washed with 100 parts of water at 100° C. and the fat centrifuged off, thereby removing almost all of the fat solids. The remaining liquid was added to another 100 parts of 2% sodium hydroxide solution (to obtain the required 1% concentration) and processed at 100° C. for 8 minutes. The remaining solid material was removed by centrifuging and straining through a 40 mesh screen (sieve opening 0.42 mm) and assayed as:

| Clean Bone | 66% (calcium 32%) |
| Protein | 8% |
| Water | 26% |
| Lipids | Trace (<0.1%) |
| Carbohydrates | Trace (<0.1%) |

The clean bone thus obtained was stored in a 25% brine solution for future use.

The liquid fraction obtained from the last-mentioned separation was neutralised with hydrochloric acid and drum dried to obtain about 18 parts of solid material of which 14 parts was protein and 4 parts salt. Alternatively, membrane dialysis could be used to obtain 14 parts of salt-free protein.

The solid chicken bone product that results is a coarse porous clean white irregular material, characterized as being of plate form. The bone was originally finely-divided in the meat/bone separation process and with the final product it is found that about 40% by weight is retained on a 10 mesh screen (sieve opening 2 mm) while 60% is retained on a 40 mesh screen with some finer particles in the 1 micron size being present; the product may therefore be characterized as being of size such that about 50% by weight is retained by a 20 mesh screen (sieve opening 0.84 mm). The following is a listing of the physical properties and microbiological and chemical analyses of materials of the invention:

The pore size of different bone materials varies widely, as determined by examination with an electron scanning microscope of samples of fish (trout), chicken, pork, lamb and beef vertebrae.

The fish bone was found to be very much more porous than any of the other and at low magnification exhibited almost a "honeycomb" structure; the pores were generally large, ovoid in shape with the major axis transverse to the length of the vertebrae, and more uniform in size than in the other bones, varying in the photograph from about 50 to 250 microns along the major axes.

The chicken bone was less porous and at low magnification had the appearance of a somewhat porous piece of pumice stone; the high magnification showed pores of from about 100 to 225 microns.

The pork bone examined showed areas of large pores adjacent to areas of small pores, the large pores being from about 100 to 220 microns in size while the small pores were about 15–35 microns in size.

At low magnification the lamb bone had the external appearance of being very porous with pores of about 100–700 microns, but the respective high magnification photograph was of a surface that accidentally was a non-porous surface, so that more accurate measurement of pore size was not possible.

Finally, the beef bone examined in this manner showed in the low magnification photograph a generally uniform but less porosity than the other bones, the section examined in the high magnification photograph being of highly irregular conformation with apertures from about 15 to 800 microns.

Proteinaceous catalyst materials and amino acids to be supported on the bone typically will have molecules of less than 1 micron size, while bacteria and yeasts will typically be of particle size in the range 1–5 microns. Clearly therefore these materials can lodge in the ores in the bone with ready access by the liquid substrate, so that the surface available for attachment is increased enormously by this porosity.

It is a particular advantage of the support materials of the invention that they are inherently sterilised during their production, without deactivation of the binding ability of the oseine, the treatment removing unwanted cellular material, bacteria and yeasts from the support material, which materials may otherwise start their own fermentations, degradations, etc. Because of the stability of the bone it is also possible to pasteurise it, if necessary, for example by a heat treatment of about 65°–75° C. for a period of about 5–30 minutes.

This temperature stability of the support material also gives the possibility of operating the catalysed process at elevated temperature, for example, at the maximum temperature for a proteinaceous enzymatic catalyst, without degradation of the support material. All catalysed systems are temperature sensitive, and the reaction rate of enzymatic systems also increases with temperature up to the temperature ($T_D$) at which it begins to become denatured. Oseine is a stable protein which will withstand a higher temperature than most enzymes. Moreover, the immobilization increases the activation energy and renders the immobilized material more stable; there is therefore the possibility that the $T_D$ temperature can be shifted into a zone in which pasteurisation occurs and repasteurisation is not needed.

Some supported materials, particularly cellular materials, are attachable directly to the surface of the support material by adsorption, including charge attraction, or by entrapment in the porous material.

Direct adsorption to a solid support material is one of the preferred methods of immobilization if feasible, because of its simplicity and low cost. Moreover, adsorption is a relatively easily reversible process which allows for ready recovery of the support material after the catalyst has been exhausted. In the case of cells this is via multipoint attachment which enables the cells to adhere to the support material much more strongly than enzymes. Cell wall composition must be considered, including its charge, the age of the cell, and the ratio between the volume of the cell and its surface area. Additionally, properties of the support material such as its composition, its surface charge, surface area and pore size play important roles. The actual charge on the support material limits the available choice of microorganisms for attachment as the adhesion phenomena is mainly based on electrostatic interactions between the charged microbial cells and the charged support material. Since electrostatic interactions are involved adsorption will be affected by pH changes that occur as the result of microbial metabolism. All cells that have been examined for attachment, including microorganisms, have a net negative charge. The charge of a cell is related to its surface ionogenic groups, which undergo dissociation according to the pH of the immediate environment, the ionization of carboxyl and amino groups according to Equations 1 and 2 below being apparently a critical reaction indicating a net positivity in highly acidic conditions and a net negativity in alkaline conditions.

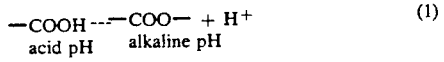

(1)

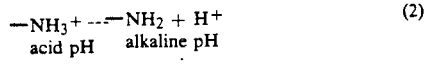

(2)

The pH values for optimum adsorption depend on the relative isoelectric points (iep) of the microbial cells. The strongest adsorption of most cells generally occurs at pH 3-6, and the majority of microorganisms studied have iep in the range of pH 2-pH 3. For example, *Leuconostoc mesenteroides* has a iep of pH 3.0. At its iep the surface charge of a bacterium will be zero while if the pH of a bacterial suspension is above the iep of the carboxyl groups, ionizable hydrogens can be produced, which can conceivably be replaced by any other cation; the entire cell thus behaves as a large anion and is capable of combining with any cation. Alternatively, at pH values below the iep of the amino groups, the bacterial cell can assimilate additional hydrogen ions; each cell will then exhibit a net positive surface charge and behave as a large cation. This charge reversal of some bacteria may not be observed except at extreme pH, e.g. less than 2.

The advantage of using a porous support material such as bone is related to the amount of surface area available because of this porosity. The following is a list of the possible forces of attraction between microbial cells and the adsorbent surfaces:

1. chemical bonding (hydrogen, thio, amide and ester bonds)
2. ion pair formation ($-NH_3^+ \ldots -OOC-$)
3. ion triplet formation ($-COO- \ldots Ca^{2+} \ldots -OOC-$)
4. interparticle bridging (polyelectrolytes)
5. charge fluctuations
6. charge mosaics
7. charge attraction of opposite signs
8. electrostatic attraction between surfaces of similar charge (same net charge but different surface potentials)
9. electrostatic attraction due to image forces
10. surface tension
11. van der Waals forces of attraction
12. electromagnetic forces
13. hydrodynamic forces
14. diffusional forces
15. gravitational forces
16. positive chemotaxis (low cellular mobility)

Less numerous are the possible forces of repulsion:

1. charge repulsion between surfaces of similar charge
2. van der Waals forces of repulsion
3. steric exclusion (hindrance)
4. negative chemotaxis (high cellular mobility)

The time required to permit cell adsorption of the cellular material to the solid support material must be considered and can be determined by monitoring the optical density of the cell suspension in the feed tank, with respect to time, during recirculation of the cell suspension over the solid support material. Maximum cell loading can be considered as having been achieved when the optical density of the cell suspension reaches a constant minimum value, for example, for a period of at least two hours, the recirculation flow rate being maintained at a level that will not cause the cells to be washed off the support material. In some procedures the cell suspension is recirculated for a determined amount of time followed by a period where the solution is allowed to stand in order to encourage maximum adsorption. The recirculating, as with agitation, increases the probability of contact between the microbial cells and adsorbent particles, but agitation can not be too long or too vigorous or it can cause desorption.

A carefully controlled drying procedure may be used to enhance adsorption by forcing a close contact between the cells and the support material surface. Starving the cells (e.g. by immersion in pure water) may be used to promote adhesion. Starvation induces a modification of the cell wall and the release of ionic substances, thereby decreasing the electrostatic repulsion between the cells and the support material. However, a decrease, or loss of metabolic activity may be observed following such treatments. Although spontaneous adsorption is preferable it does not always occur, and to enhance the adsorption by decreasing repulsion or enhancing electrostatic attraction between cells and the support materials, the support or the cell surface may be coated with a layer of positively charged colloidal particles such as Al(OH)$_3$ or Fe$_2$O$_3$, or metallic ions (Fe$^{3+}$, Al$^{3+}$).

Adsorbtion may also be used for the attachment of appropriate enzymes and other large-molecule chemical catalysts. Immobilized cells have several advantages over immobilized enzymes, in that it is not necessary to previously have extracted the enzyme from the cell. Furthermore, heat and operational stability in continuous enzyme reactions using intact cells are the same as, or superior to, those of immobilized enzymes. One disadvantage of using immobilized cells is that several different enzymes are usually in the cells and they may initiate side-reactions or degradation of the desired product. This can often be avoided by heat, acid and/or chemical treatment before or after immobilization of microbial cells.

Entrapment is based on the inclusion of the supported material within the rigid network constituted by the porous support material to prevent its diffusion into the surrounding medium, while still allowing penetration of the support material by the reacting fluid. Within this three dimensional network, the material is free in the compartments and pores.

Whereas the adsorption and entrapment methods are particularly applicable to the immobilization of living cells, covalent coupling is more appropriately used with dead cells or cells to be utilized for only a single catalytic step. Covalent coupling methods have an advantage over the other methods by reducing or eliminating the problem of release or desorption of cells from the support material, and while successfully used for enzyme immobilization, the attachment of whole cells to surfaces requires binding agents which generally are toxic toward the cells. Viable cells immobilized in this manner divide and form new unbound cells, resulting in substantial cell leakage. The binding agents also represent an added cost.

Some catalytic agents may be attachable directly chemically to the oseine, but it is a relatively stable non-reactive protein and preferably is activated by use of a cross-linking agent, which will attach itself chemically to the oseine and provide a free bond for attachment of the catalyst. One such bi-functional cross-linking agent for use with enzymatic catalysts is glutaraldehyde which will provide a free aldehyde group for chemical attachment of the enzyme cell or biological reagent. In a typical procedure the cleaned finely-divided bone is immersed in an aqueous solution of the glutaraldehyde of concentration about 2% by volume for a period of about 10 minutes at a pH in the range 5.5 to 6.5. Concentrations of from 0.1% to 25% can be employed, and pH in the range from 3 to 10. The bone is then water washed two or three times to free it of excess glutaraldehyde and immersed in a solution of the required enzyme.

Other cross-linking agents that have been employed are:

Cyanogen bromide,
Hydrazine,
Carbodiimide,
and
Woodward's reagent K*

*N-ethyl-5-phenylisoxazolium-3-sulphonate sold by Sigma Biochemicals

Glutaraldehyde has the advantages of it's convenience in use, water solubility, ready availability and relatively very low toxicity.

The support material of the invention has been employed for the support of the enzymes catalase; $\beta$-galactosidase (lactase); pectinases; porcine pepsin; glucose oxidase and glucose isomerase. It is found with some enzymes that account must be taken of the negative ionic effect of the calcium present in the crystalline portion of the bone; for example, pectinase will respond to the available calcium ion and gell, rendering it ineffective for enzymatic action. This effect can be reduced or avoided by "masking" the calcium, for example, by pretreatment with a calcium chelating agent, such as ethyldiaminetetraacetate (EDTA) or alginic acid; or a buffering agent such as sodium citrate and phosphates. The use of a buffering agent also provides the possibility of readily controlling the concentration of the enzyme on the support material and thus it's specific activity, which can be adjusted to suit the application for which it is employed and perhaps avoid unnecessary provision of the costly material. In a specific example, the bone was treated with the buffer solution in the ratio of 10 mL of buffer per gram of bone, and pectinase enzyme then applied in the concentration of 1 mg per mL of buffer; the resultant activated support material showed activity of 10 mg of enzyme per 150 mg of oseine.

A series of tests were performed to evaluate different methods of attachment of well-known enzymes to chicken bone, the specific enzymes employed being:

Candida utilis invertase;
porcine stomach pepsin;
Aspergillus niger pectinase;
Lactozym (Trade Mark) 3000 L type HP (lactase) of Novo Industries; and
bovine liver catalase The enzyme activity of the invertase was measured by reducing group evolution using 2-cyanoacetamide.

Milk clotting activity of the pepsin preparation was measured by timing the initial curd development of reconstituted skim milk (1:10 by volume) in 0.2M acetate buffer at pH 5.8, the activity being expressed as the reciprocal of clotting time in minutes (or milk clotting units) at 25° C.

Pectinase activity was measured as with the invertase. Lactase ($\beta$-galactosidase) activity was measured using o-nitrophenyl-D-galactopyranoside. The activity of the catalase was measured by the initial rate of oxygen evolution in the presence of 0.5 mM hydrogen peroxide in 0.5M citrate-phosphate buffer at pH 5.0 using an oxygen polarograph.

Enzymatic activity on the bone is expressed in units per gram of dry bone; one unit of activity results in 1u mol of substrate at 25° C. being reacted per minute.

Adsorbtion without any pretreatment was achieved through the addition of the enzyme in an appropriate buffer to the clean dry bone followed by incubation under vacuum for 1 hour and 0° C. Excess enzyme was removed by exhaustive washing with buffer fluid prior to determination of the enzymatic activity. The same procedure for addition to the support material was also employed after the respective pretreatment. The respective buffers used were:

Invertase: 0.05M acetate at pH 4.4
Pepsin 0.5M citrate at pH 4.2
Pectinase: As invertase
Lactase 0.2M phosphate at pH 6.5 with 2 mM magnesium chloride at 5 mM cysteine Catalase : 0.1M phosphate-citrate at pH 7.0

Acyl-azide cross-linking (derivitisation), glutaraldehyde derivitisation, with or without silanization, carbodiimide derivitisation and silanization were carried out as described elsewhere herein.

Treatment with collagenase to develop active sites prior to the addition of glutaraldehyde was carried out by incubating the bone in 0.2% (w/v) collagenase in 0.2M phosphate buffer at 20° C. (room temperature) for 8 hours. The results of the tests are given in Table 1 below:

TABLE 1

| Enzyme | Immobilization Method | Initial Enzyme Activity in Immobilizing Solution U | Activity on Bone U/g |
|---|---|---|---|
| Invertase | Adsorption | 143 | 2.3 |
| | Acyl-Azide | 104 | 38 |
| | Glutaraldehyde (GHD) | 64 | 4.4 |
| | Carbodiimide | 28 | 1.0 |
| Pepsin | Adsorption | 43 | 0.68 |
| | Acyl-Azide | 38 | 0.63 |
| Pectinase | Acyl-Azide | 28 | 0.11 |
| | Glutaraldehyde (GHD) | 32 | 0.27 |
| | Carbodiimide | 30 | 0.10 |
| Lactase | Adsorption | 12 | 0.12 |
| | Acyl-Azide | 12 | 0.11 |
| | Glutaraldehyde (GHD) | 12 | 0.03 |
| | Silanized GHD | 24 | 0.10 |
| | Collagenase GHD | 24 | 0.16 |
| Catalase | Adsorption | 128 | 0.60 |
| | Acyl-Azide | 128 | 0.88 |

It will be seen that with the tests performed the most effective methods of attachment were adsorption and covalent coupling by acyl-azide. With catalase the acyl-azide system was superior to adsorption, while the reverse is true for lactase. The uniformly superior results for invertase will be noted, and also the uniformly good results for acyl-azide as compared to gluteraldehyde. The latter requires free amino groups which are not abundant in the collagenous oseine, so that the former using carboxylic acid and hydroxyl functional groups has more available sites. It will be noted however that with lactase the silanization pretreatment to develop free hydroxyl groups, and the collagenase pretreatment to liberate free amino groups, both raise the activity with glutaraldehyde to above that achieved with acyl-azide. Difficulty was experienced in evaluating the activity of the pectinase owing to gelling of the citrus pectin substrate, perhaps due to the high calcium level in the bone as described above, or contamination of the stock of enzyme.

The low yields of activity observed are believed to be indicative primarily of the relatively small number of active sites available, but the ready availability and economy of preparation of the granular bone material offers advantages over conventional support materials. The results of a study on flow characteristics of a granular bone column are given below. The application of the material to the support of pepsin has shown that in a sequential batch reactor system for the clotting of milk over 200 times the volume of the bed can be processed without loss of flow capacity or curd yield. Milk is a colloidal fluid food material which, because of its high content of large fat and protein molecules, chronically causes fouling of conventional support materials. An inexpensive securely-supported, high flow rate, long-life system cannot therefore be compared directly by these tests where the values for initial enzyme activity would involve total loss of enzyme in a single batch reaction.

It is common in some known immobilization systems to use filler material mixed with the support material, to improve flow characteristics and/or to extend the expensive support material, but this is not normally necessary with the support materials of the invention owing to their inherent structure and relatively low cost. It is unlikely therefore that the supported material used normally constitute more than 0.25–5% by weight of the total of support material plus supported material. For example, in the case of yeasts which are inherently large and bulky and also grow on the support material, by the time that its weight has reached 5% of the total all of the cells would no longer adhere to the support material, and the excess would no longer be immobilised. In the case of bacteria even if densities as high as $10^{10}$ per gram of support material could be achieved the total weight of the bacteria would still be less than 1% by weight of the total.

Another series of tests were carried out to compare the effectiveness of different immobilization systems using some of the above cross-linking agents, as follows:

IMMOBILIZATION WITH THE USE OF GLUTARALDEHYDE 1.0 g of chicken bone was suspended in 5 ml of 2 wt. % glutaraldehyde solution in a 0.1M sodium phosphate buffer at pH 6.5. The mixture was kept under vacuum at room temperature for 30–60 min. The glutaraldehyde was removed and the treated bone was washed with distilled water. The bone was then treated with 5 m. of 0.05M acetate buffer solution at pH 4.4, containing varying amounts of polygalacturonase or invertase. Immobilization proceeded at standard conditions of 0°–4° C. for one hour under vacuum. The enzyme solution was then decanted and the bone washed thoroughly with acetate buffer (0.05M, pH 4.4) and stored in the same buffer.

IMMOBILIZATION USING HYDRAZINE 10 g of chicken bone was added to 15 ml of 0.05% (w/v) hydrazine sulphate solution in a 0.2M sodium phosphate buffer at pH 7.0 and the suspension incubated at room temperature for 12 hours under vacuum. The hydrazine solution was then decanted and the bone thoroughly rinsed with 0.1 mM sodium chloride. The acyl-hydrazide bone was treated at 0° C. with 10 ml of both 0.6N HCl and 1M sodium nitrite for 3–5 min. The nitrite was rinsed out with 250 ml of each of 0.1M sodium chloride and 1 mM HCl. The bone was then resuspended in 15ml of solution of 0.05M acetate buffer and pH 4.4, containing varying amounts of polygalacturonase or invertase. Enzyme coupling proceeded at standard conditions of 0° C. for 3 hour under vacuum. The enzyme coupling solution was decanted and the bone thoroughly washed with acetate buffer (0.05M, pH 4.4) and stored in the acetate buffer.

IMMOBILIZATION WITH WOODWARD'S REAGENT K 300 mg of the Reagent K was added to a suspension of 1 g of bone in 5 ml of 0.1M sodium phosphate buffer and pH 8.3. The reaction mixture was held under vacuum at room temperature for 1 hour. The solution of Reagent K was withdrawn and the bone rinsed thoroughly with distilled water. The treated bone was immersed with 5 ml of 0.05M acetate buffer containing varying concentrations of invertase. The mixture was magnetically stirred overnight at 4° C. The enzyme coupling solution was removed and the enzyme-treated bone was washed completely with acetate buffer (pH 4.4, 0.05M), the bone being stored in 0.05M acetate buffer at pH 4.4.

IMMOBILIZATION USING CARBODIIMIDE (CYANAMIDE)

100 mg of cyanamide was added to a suspension of 1 g of bone as described above in 5 ml of 0.1M sodium phosphate buffer of pH 7.0. The mixture was maintained under vacuum for 15-30 min. at room temperature. After extracting the carbodiimide solution, the bone was rinsed with distilled water. The treated bone was placed in 5 ml of 0.05M sodium acetate buffer at pH 4.4 containing polygalacturonase or invertase at varying concentrations. Enzyme attachment proceeded at standard conditions of 0°-4° C. for 30 min. under vacuum. The enzyme solution was decanted and the bone washed thoroughly with the acetate buffer and stored in the same buffer.

IMMOBILIZATION USING CYANOGEN BROMIDE 5 g of cyanogen bromide was added to a suspension of 25 g of bone in 200 ml of distilled water. While stirring, 1M KOH was added dropwise to maintain the pH between 9.5-10.5. After 10 min. the cyanogen bromide solution was withdrawn and the bone washed with sodium bicarbonate at pH 8.0. The bone was immediately resuspended in 25 ml of 0.05M acetate buffer at pH 4.4, containing polygalacturonase at concentrations used previously. Enzyme coupling proceeded at 0°-4° C. overnight under vacuum. When immobilization was completed, the treated bone was handled as before.

ENZYME ACTIVITY ASSAYS

The activity of both polygalacturonase and invertase was assayed spectro-photometrically using the method of Gross (1982), a modification of the 2-cyanoacetamide procedure of Honda et al. (1982). The assay was based upon the enzyme-catalyzed hydrolytic release of reducing groups, galacturonic acid, and glucose and fructose by polygalacturonase and invertase respectively. Upon reacting 2-cyanoacetamide with reducing carbohydrates, ultraviolet-absorbing products were formed which could be determined.

Polygalacturonase activity was measured as follows. To 2.0 ml of 1% (w/v) polygalacturonic acid in 0.05M acetate buffer (pH 5.0), samples of bone immobilized with enzyme, of decanted enzyme coupling solution or of soluble enzyme possessing polygalacturonase activity were added. The reaction proceeded while stirring for the given reaction period (1-10 min). The reaction mixture (2 ml) was poured into a large test tube containing 10 ml of 0.1M borate buffer, pH 9.0, to which was added 2 ml of 1% (w/v) 2-cyanoacetamide. Samples were mixed and immersed in a boiling water bath for 10 min. After equilibriation to 25° C. in an ice bath, the absorbance of the samples was read at 276 nm. The calibration curve was constructed using solutions of galacturonic acid containing 5-750 nm of galacturonic acid per volume of sample to be assayed. One unit of polygalacturonase was defined was that amount of enzyme required to liberate one micromole of galacturonic acid from the polygalacturonic acid solution at 25° C.

Invertase was determined similarly but with some modifications. To 5 ml of 0.05M sucrose solution in 0.05M acetate buffer, pH 5.0, a sample of bone immobilized with invertase, of decanted enzyme coupling solution, or of soluble enzyme possessing invertase activity was added. As the reaction progressed with agitation, aliquots of 0.4 ml were removed and added to a test tube that contained 2 ml of 0.1M borate buffer, pH 9.0. After 0.4 ml of 1% (w/v) 2-cyanoacetamide was added, samples in test tubes were mixed and immersed in a boiling water bath for 10 min. After cooling to 25° C., the absorbance was measured at 276 nanometers. The calibration curve was constructed using equimolar solutions of glucose and fructose containing 5-1000 nanomols of each per 0.4 ml. One unit of invertase was defined as that amount of enzyme required to liberate one micromole of glucose in one minute from a sucrose solution at 25° C.

The following Tables 2 and 3 show the results of the different methods, and it is evident that glutaraldehyde was the best method of the techniques studied for immobilizing polygalacturonase, but the hydrazine technique was best of those examined for the attachment of invertase with the glutaraldehyde method producing lower but still favourable yields No measurable activity was found on the bone treated with polygalacturonase using cyanogen bromide.

TABLE 2

ACTIVITY OF IMMOBILIZED POLYGALACTURONASE USING DIFFERENT METHODS

| Method * | Concentration of enzyme in coupling sol'n (mg/g dry bone) | Activity on bone (Units/g dry bone) | Yield as % of Soluble Activity ** |
|---|---|---|---|
| Glutaraldehyde | 11.07 | 0.266 | 1.10 |
| Hydrazine | 9.89 | 0.112 | 0.42 |
| Carbodiimide | 10.44 | 0.102 | 0.406 |
| Woodward's K | 8.02 | 0.096 | 0.436 |
| Cyanogen bromide | 8.50 | 0.0 | 0.0 |

TABLE 3

ACTIVITY OF IMMOBILIZED INVERTASE USING DIFFERENT METHODS

| Method * | Concentration of enzyme in coupling sol'n (mg/g dry bone) | Activity on bone (Units/g dry bone) | Yield as % of Soluble Activity ** |
|---|---|---|---|
| Glutaraldehyde | 0.40 | 4.43 | 7.04 |
| Hydrazine | 0.04 | 22.7 | 42.51 |
| Carbodiimide | 0.174 | 0.948 | 3.067 |

** Activity of polygalacturonase - 2.9 Units $mg^{-1}$ and activity of invertase - 160 Units $mg^{-1}$ (soluble).

The following Table 4 shows the effect of the pH of the coupling solution on the activity of immobilized invertase using hydrazine cross-linking agents.

TABLE 4

| Initial pH of Coupling | Final pH of Coupling | Activity (U/g dry bone) |
|---|---|---|
| 4.4 | 6.1 | 25.60 |
| 5.0 | 6.6 | 16.93 |
| 5.6 | 6.8 | 11.33 |

The following Table 5 shows the effect of the enzyme coupling time on the activity of immobilized invertase using hydrazine.

TABLE 5

| Coupling Agent | Time of Coupling (hr) | Activity (U/g dry bone) |
| --- | --- | --- |
| Glutaraldehyde | 1.0 | 21.30 |
|  | 2.0 | 21.02 |
| Hydrazine | 2.3 | 25.60 |
|  | 3.0 | 23.95 |
|  | 3.7 | 26.25 |

The following Table 6 shows the effect of invertase concentration in the coupling solution on the activity of immobilized invertase using hydrazine.

TABLE 6

| Concentration (mg/g dry bone) | Activity (U/g dry bone) | Yield (% of soluble activity) |
| --- | --- | --- |
| 0.17 | 1.95 | 6.98 |
| 0.40 | 4.43 | 7.04 |
| 0.84 | 9.66 | 7.21 |
| 1.0 | 21.3 | 13.31 |
| 1.8 | 21.02 | 7.3 |

The effect of the pH of the coupling solution was that the activity of the immobilized invertase decreased as the pH of the enzyme coupling solution increased. This was likely the result of invertase inactivation caused by increases in the pH of the coupling solution during the immobilization as indicated in Table 4. The activity was not affected by coupling time as shown by the results in Table 5. This suggested that for a given enzyme concentration coupling took place immediately when the enzyme was introduced and possible saturation of enzyme coupling sites occurred within 1 and 2.3 hrs respectively using glutaraldehyde and hydrazine respectively. The activity was however affected by enzyme concentration in the coupling mixture. The results obtained reveal that activity of the immobilized invertase is directly related to the amount of available enzyme It can be seen that approximately 7% of the enzyme was bound in most cases.

A further series of tests were carried out for the enzyme lactase alone to compare the effectiveness of different methods of immobilization, as set out in Table 7 below. Cross linking with glutaraldehyde was carried out both sequentially and simultaneously, and the sequential system was subjected to two different drying protocols, and employed also with silanization and pretreatment with collagenase to develop additional active sites.

In single stage drying the initially dry bone was incubated with 2% GHD in sodium phosphate buffer and pH 6.0 for 1 hour. The GHD-treated bone was washed exhaustively with distilled water, following which 5.0 ml of enzyme solution (2.4 units/ml) were added. The mixture was held at 0° C. for 2.75 hours. After washing thoroughly with buffer the enzyme activity on the bone was determined as above. The procedure employed for two stage drying was as for single stage except that the washed, GHD-treated bone was oven-dried prior to the addition of the enzyme. The immobilization process involved the incubation of about 1 g of dry, GHD-treated bone with 12 units of enzyme activity for 1 hour at 0° C.

Silanizing prior to the GHD cross-linking was carried out by treating about 5 g of dry bone for 3 hours at room temperature with a 0.4% solution of 3-aminopropyltriethoxysilane (8-APTES). The bone was then rinsed ten times with deionized water, and oven-dried. Immobilization involved the incubation of about 2 g of dry, silanized bone with 10 ml of 2% buffered GHD and pH 5.5). Following rinsing with sodium phosphate buffer at pH 5.5, 10 ml of enzyme solution (2.4 units/ml) were added, and the mixture was allowed to react at 0° C. for 90 minutes After thorough washing with buffer, the level of enzyme activity was determined.

The collagenase treatment involved the use of a buffered 0.2% solution at pH 7.0 of Clostridium histolyticum collagenase, the mixture being reacted overnight at 37° C. The bone was washed free of collagenase using distilled water, and oven-dried prior to treatment with GHD. Ten ml of enzyme solution (2.4 units/ml) were added to about 6 g wet, GHD-activated bone. Coupling proceeded for 90 minutes at 0° C. The enzyme-treated bone was then exhaustively washed with buffer solution.

Adsorption involved the incubation of about 2 g dry, untreated bone with 5.0 ml of enzyme solution (2.4 units/ml). Coupling proceeded for 1 to 2 hours at 0° C. under vacuum.

The immobilization yields, in terms of units of enzyme immobilized per gram of support bone (absolute yield), were found to vary widely with the method of immobilization employed. The Table 7 below lists the immobilization methods used.

TABLE 7

| Method | Units/g Bone | % Yield |
| --- | --- | --- |
| Adsorption | 0.124 | 9.9 |
| Hydrazine | 0.072 | 3.1 |
| GHD regular (sequential) | 0.019 | 0.4 |
| GHD − 2 point drying | 0.007 | 1.7 |
| GHD − 1 point drying | 0.035 | 1.0 |
| GHD + Silanization | 0.068 | 4.4 |
| GHD + Collagenase | 0.108 | 2.8 |
| GHD (simultaneous) | 0.005 | 0.1 |
| Woodward's Reagent K | 0.027 | 0.3 |
| CNBr Coupling | 0.012 | 0.1 |

As with the other tests the hydrazine and adsorption systems gave excellent results, with comparable results from the prior silanization and collagenase treatments.

The differences must be noted for the results of the regular (sequential) GHD treatment, and those obtained when similar experiments were conducted with the support material being dried at particular points during the immobilization process, and these appear to show that reaction with the bone is hindered in the presence of moisture. Thus, the use of initially dry bone may allow for maximum exposure of the reactants to the bone surface. Furthermore, using dry bone, there is no dilution effect due to moisture at the surface, such a dilution effect would be quite pronounced due to the small sample sizes employed.

Another application of the material of the invention is in the field of affinity chromatography in which a fluid mixture to be assayed is passed through a column in which specific coupling reactions take place between constituents of the fluid and the material of the column The usual prior art media for this procedure are various gels which are only capable of slow elution. The porous bony material of the invention provides for rapid passage of the fluid through the column. When the required couples have been formed the column is washed to remove unwanted material. The wanted couples can then readily be uncoupled by rendering the support material sufficiently acid, and washed out from the column. Such procedures are particularly suited for the separation of highly complex and delicate molecules such as antigens. With the support materials of the invention it is possible to attach the required coupling agents to the oseine and because of its stable and highly porous nature obtain much faster eleution times.

FLOW CHARACTERISTICS

Tests were carried out to compare the pressure drop characteristic of unidirectional fluid flow through a packed bed of the chicken bone support material of invention, as compared with the drop through the same column of 'Dowex' ion-exchange resin (Lot No. MM-12141-Al) manufacturered by Dow Chemical Co., Midland, Mich. The bed chamber consisted of 2.9 cm inside diameter pipe of methyl methacrylate resin, the total depth of the bed being 19.5 cm with a bed depth of 15.1 cm between upstream and downstream pressure measuring outlets. The pressure differential was measured using a mercury U-tube manometer, while the flow rates were measured by collecting the liquid that passed through the bed in a two liter cylinder, tap water being employed as the liquid and being fed to the packed bed at different flow rates.

The bed was packed so that settling was avoided during the tests, and to insure a constant porosity during the test run, an initial flow was maintained at the maximum operating pressure drop to compact the bed until no further change in porosity was detected. The bed was not disturbed until all flow tests were completed. The Reynolds number of the fluid was varied by varying the flow rate.

The pressure drops were measured to an accuracy of 0.5 mm of Hg, the data being corrected by subtracting the pressure drop in the empty bed and fittings. The equivalent particle diameter of the chicken bone was taken as the average of the opening sizes of 10 and 20 mesh sieves, namely 1.246 mm, its bulk density being 495.6 kg/m$^3$. The corresponding equivalent particle size of the resin was 0.635 mm, while its bulk density was 462 kg/m$^2$.

Table 8 below tabulates the experimental data from which it will be seen that the chicken bone has much less pressure drop as compared to that through the ion exchange resin. For example at Re=19.3 for the bone the pressure drop is 21.2, while at Re=20.1 for resin the pressure drop is 224.3, an increase of more than 10 times. The value P/V is found to be approximately linear for both the bone and the resin and the consistently higher value for the resin is apparent from the Table.

TABLE 8

| FLUID FLOW AND PRESSURE DROP DATA | | | |
|---|---|---|---|
| Flow rate (V) (1 · m$^{-2}$ · s$^{-1}$) | Pressure drop (P) (kPa/m bed) | Reynolds No. (Re) | P/V |
| BONE | | | |
| 11.2 | 13.3 | 15.0 | 1.18 |
| 14.4 | 21.2 | 19.3 | 1.47 |
| 28.4 | 44.2 | 38.1 | 1.55 |
| 29.0 | 49.4 | 39.0 | 1.70 |
| 29.0 | 47.2 | 39.0 | 1.62 |
| 42.3 | 80.3 | 56.8 | 1.90 |
| 43.1 | 84.8 | 57.8 | 1.96 |
| 46.0 | 91.8 | 61.7 | 1.99 |
| 48.6 | 98.0 | 65.2 | 2.01 |
| 51.2 | 112.1 | 69.2 | 2.19 |
| RESIN | | | |
| 11.6 | 106.0 | 7.9 | 9.1 |
| 19.1 | 186.3 | 13.1 | 9.75 |

TABLE 8-continued

| FLUID FLOW AND PRESSURE DROP DATA | | | |
|---|---|---|---|
| Flow rate (V) (1 · m$^{-2}$ · s$^{-1}$) | Pressure drop (P) (kPa/m bed) | Reynolds No. (Re) | P/V |
| 22.2 | 191.6 | 15.2 | 8.63 |
| 26.2 | 204.0 | 17.9 | 7.78 |
| 29.3 | 224.3 | 20.1 | 7.65 |
| 33.8 | 260.5 | 23.1 | 7.70 |
| 34.7 | 281.7 | 23.7 | 8.11 |

OTHER APPLICATIONS

The support materials of the invention can of course be employed in any process in which the bone matrix is not appreciably degraded by the conditions of operation, and are particularly applicable to enzyme systems, since the support material will usually have much greater tolerance of the operating conditions than will the enzyme itself. Owing to the by-product nature of poultry bone its cost is relatively low and the ease with which enzymes can be immobilised on the protein component renders it highly functional. Examples of suitable applications are:

a. The support of lactase enzyme for the continuous treatment of whey streams from cheese production to convert the lactose to galactose and glucose. A subsequent galactase enzyme would convert all the galactose to glucose which could be utilized as a support for the growth of yeast to produce alcohol or of lactic or acetic acid bacteria to produce food grade acidulants.

b. The support of glucose isomerase enzyme for the production of high fructose syrups as liquid sweeteners.

c. The support of pectinases for the clarification of fruit juices.

d. The support of proteases for the continuous "chill-proofing" of beer.

e. The support of specific proteases, like chymosin, for the continuous rennetting of milk in the production of cheese.

f. The support of chicken pepsin on chicken bone support material for use in continuous rennetting in cheese production.

g. The support of glucose oxidase for the removal of glucose from egg white prior to freezing and drying.

h. The support of lipases for the production of specific fatty acids and interesterification of triglycerides.

i. The support of lactic acid bacteria, such as *Leuconostoc oenos*, in malolactic fermentation of wine for the fermentation conversion of L-malic acid to L-lactic acid and carbon dioxide. This is a secondary fermentation that usually occurs spontaneously after the alcoholic fermentation has been completed, and is required with wines from cooler climates to reduce acidity and provide stability after bottling. The necessary bacteria are present on the grape skins and perhaps also the processing vessels but with modern cleaner processing and requirement for reduced processing times there is no longer adequate time for the reaction to proceed, especially since the bacteria grow only slowly in the harsh conditions of wine with pH 3-3.8, alcohol content 10-14%, sulphur dioxide content of 10–100 ppm and low content of residual sugar. Inoculation is sometimes successful, but a safer approach is the use of a column reactor with the bacteria supported therein on a bone substrate of the invention. It is found that direct absorption is possible with a predicted effectiveness of 99% at 22.5° C. for 42 minutes and pH 3.85. It maybe noted that the bone alone will reduce the malic acid content of the wine by 40 to 70%, it is believed by binding with the calcium in the bone.

j. The support of lactase, the lactose-splitting enzyme $\beta$-galactosidase, the action of which produces a milk product, such as fluid milk or whey, which possesses more desirable chemical and physical characteristics than its untreated counterpart More specifically, low-lactose milk would benefit persons who suffer from lactose intolerance (inability to digest lactose) and who normally refrain from consuming dairy products Furthermore, lactose-hydrolyzed (LH) milk would be useful in the preparation of concentrated milk products where lactose crystallization causes textural problems. The development of a stable, immobilized lactase would also be of use in the treatment of whey and thereby aid in the abatement of the whey disposal problem currently faced by many cheese processing plants.

I claim:

1. An immobilization support material for use in chemical or physical processes for support thereon of supported material, the support consisting of finely-divided animal bone comprising a collagenous matrix of organic fibrous connective tissue material including osein having uniformly distributed therethrough mineral hydroxyapatite, the bone having external surfaces and having internal surfaces provided by internal pores and Haversian canals therein, from the external surfaces of which bone external tissue has been removed, and from the internal surfaces of the internal pores and Haversian canals internal tissue has been removed by dissolving it therefrom, wherein the collagenous matrix is exposed and provides sites for the support thereon of the material to be supported, the cleaned bone containing not more than 0.5% by weight of remaining lipid material.

2. An immobilization support material as claimed in claim 1, wherein the cleaned bone contains not more than 0.1% by weight of remaining lipid material.

3. An immobilization support material as claimed in claim 2, wherein the bone particle size is in the range 0.1–2 mm.

4. An immobilization support material as claimed in claim 2, in combination with a chemical cross-linking agent for the collagenous matrix and the material to be supported thereon.

5. An immobilization support material as claimed in claim 4, wherein the chemical cross-linking agent is selected from the group consisting of glutaraldehyde, cyanogen bromide, hydrazine, carbodiimide, and Woodward's Reagent K.

6. An immobilization support material as claimed in claim 2, wherein the animal bone is poultry bone.

7. An immobilization support material as claimed in claim 2, in combination with catalytic material supported thereon.

8. An immobilization support material as claimed in claim 7, wherein the catalytic material consists of from 0.25% to 5% by weight of the total of immobilization support material and catalytic material.

9. An immobilization support material as claimed in claim 7, wherein the catalytic material is an enzymatic material selected from the group consisting of cells and the enzymes catalase, $\beta$-galactosidase, pectinase, lipase, glucose oxidase, glucose isomerase, galactase and protease.

10. An immobilization support material as claimed in claim 2, wherein the support material is rendered alkaline to produce a positive charge thereon, and in combination with supported material attached by charge attraction.

11. An immobilization support material as claimed in claim 2, in combination with supported material attached by adsorption.

12. An immobilization support material as claimed in claim 2, in combination with supported material, wherein the immobilization support material has been dried to a moisture content of less than 10% before attachment of the supported material thereto.

13. An immobilization support material as claimed in claim 2, wherein osein of the collagenous matrix has been treated with collagenase enzyme to develop attachment sites thereon for attachment of supported material.

14. An immobilization support material as claimed in claim 2, in combination with supported material, wherein the surfaces of the immobilization support material are positively charged to promote attachment of the supported material to the surfaces.

15. A method of making an immobilization support material for support thereon of supported material for chemical and physical processes, the immobilization support material consisting of finely divided animal bone comprising a collagenous matrix of organic fibrous connective tissue material including osein having uniformly distributed therethrough mineral hydroxyapatite, the bone having external surfaces and having internal surfaces provided by internal pores and Haversian canals therein, the method comprising removing external tissue from the external surfaces of finely divided animal bone, and removing internal tissue from the internal surfaces of the pores and Haversian canals by dissolving it therefrom to result in cleaned bone containing not more than 0.5% by weight of remaining lipid material, wherein the collagenous matrix is exposed to provide sites for the support thereon of material to be supported.

16. A method as claimed in claim 15, wherein the cleaned bone contains not more than 0.1% by weight of remaining lipid material.

17. A method as claimed in claim 16, wherein the bone is of particle size in the range 0.1–2 mm.

18. A method as claimed in claim 16, including the step of attaching to the immobilization support material a chemical cross-linking agent for the collagenous matrix and the material to be supported thereon.

19. A method as claimed in claim 18, wherein the chemical cross-linking agent is selected from the group consisting of glutaraldehyde, cyanogen bromide, hydrazine, carbodiimide, and Woodward's Reagent K.

20. A method as claimed in claim 16, wherein the bone is poultry bone.

21. A method as claimed in claim 16, including the step of attaching to the immobilization support material a catalytic material for support thereon.

22. A method as claimed in claim 21, wherein the catalytic material is an enzymatic material selected from the group consisting of cells and the enzymes catalase, β-galactosidase, pectinase, lipase, glucose oxidase, glucose isomerase, galactase and protease.

23. A method as claimed in claim 21, wherein the catalytic material consists of from 0.25% to 5% by weight of the total of immobilization support material and catalytic material.

24. A method as claimed in claim 16, including the step of heating the immobilization support material to a temperature of about 65° C.-75° C. for a period sufficient to cause pasteurisation thereof.

25. A method as claimed in claim 16, wherein the bone is washed with a solution of caustic soda of about 0.25% to 10% concentration to dissolve internal tissue from the bone internal surfaces.

26. A method as claimed in claim 16, including the step of attaching material to be supported to the immobilization support material, and wherein the immobilization support material is rendered alkaline to produce a positive charge thereon and the material to be supported is attached by charge attraction.

27. A method as claimed in claim 16, including the step of attaching material to be supported to the immobilization support material, and wherein the supported material is attached by adsorption.

28. A method as claimed in claim 16, including the step of attaching material to be supported to the immobilization support material, and wherein the immobilization support material is dried to a moisture content of less than 10% before attachment thereto of the material to be supported.

29. A method as claimed in claim 16, including the step of treating the osein of the collagenous matrix with collagenous enzyme to develop attachment sites thereon for material to be supported thereon.

* * * * *